US005737506A

United States Patent [19]
McKenna et al.

[11] Patent Number: 5,737,506
[45] Date of Patent: Apr. 7, 1998

[54] ANATOMICAL VISUALIZATION SYSTEM

[75] Inventors: Michael A. McKenna, Cambridge; David T. Chen, Somerville, both of Mass.; Steven D. Pieper, Thetford Center, Vt.

[73] Assignee: Medical Media Systems, West Lebanon, N.H.

[21] Appl. No.: 457,692

[22] Filed: Jun. 1, 1995

[51] Int. Cl.$^6$ .................................................. G06T 7/40
[52] U.S. Cl. ................................ 395/125; 395/127
[58] Field of Search .................................... 395/118, 119, 395/125, 129, 130, 127

[56] References Cited

U.S. PATENT DOCUMENTS

| | | | |
|---|---|---|---|
| 4,722,056 | 1/1988 | Roberts et al. | 364/413 |
| 4,729,098 | 3/1988 | Cline et al. | 364/414 |
| 4,882,679 | 11/1989 | Tuy et al. | 364/413.22 |
| 4,922,909 | 5/1990 | Little et al. | 128/630 |
| 4,945,478 | 7/1990 | Merickel et al. | 364/413.22 |
| 4,965,844 | 10/1990 | Oka et al. | 382/44 |
| 4,985,855 | 1/1991 | Aldrich et al. | 364/522 |
| 4,989,083 | 1/1991 | Eino | 358/107 |

(List continued on next page.)

OTHER PUBLICATIONS

Kawata et al., "Three-Dimensional Imaging Of Blood Vessels Using Cone-Beam CT", IEEE Comput. Soc. Press, Proceedings ICIP-94, vol. 2, pp. 140–144.

Klein et al., "Identifying Vascular Features With Orientation Specific Filters And B-Spline Snakes", IEEE Comput. Soc. Press, Computers in Cardiology 1994, pp. 113–116.

Chen et al., "Left Ventricle Global Motion And Shape From CT Volumetric Data", IEEE Apr. 1993, pp. V–101 to V–104 (reprint).

VanRoden, "Don't Look Now, But a Body Has Been Found in the Basement of Cummings Hall", Dartmouth Thayer School of Engineering Directions, a periodical published by the Trustees of Dartmouth College, Hanover, New Hampshire, vol. 8, No. 1, Fall 1993, pp. 30–36.

Roberts et al., "A frameless Stereotaxis integration of computerized tomographic imaging and the operating microscope", J. Neurosurg./vol. 65/Oct., 1986, pp. 545–549.

Weisburn et al., "An interactive graphics editor for 3D surgical simulation", SPIE vol. 626 medicine XIV/PACS IV (1986), pp. 483–490.

Shaley et al., "Pseudo–3D imaging with DICON–8", SPIE vol. 555 Medical Imaging and Instrumentation '85 (1985), pp. 63–66.

Fowler, "Computers May Drive Revolution in Neurosurgery Techniques", Washington Post, Science, 15 Aug. 1994.

Applicants' "IRS Magaziner Demo (SEE™)", displayed Jun. 1993 (24 minutes).

*Primary Examiner*—Phu K. Nguyen
*Assistant Examiner*—Cliff N. Vo
*Attorney, Agent, or Firm*—Pandiscio & Pandiscio

[57] ABSTRACT

An anatomical visualization system includes a first database that includes a plurality of 2-D slice images generated by scanning a structure. The 2-D slice images are stored in a first data format. A second database is also provided that comprises a 3-D computer model of the scanned structure. The 3-D computer model includes a first software object that is defined by a 3-D geometry database. Apparatus are provided for inserting a second software object into the 3-D computer model so as to augment the 3-D computer model. The second software object is defined by a 3-D geometry database, and includes a planar surface. Apparatus for determining the specific 2-D slice image associated with the position of the planar surface of the second software object within the augmented 3-D computer model are provided. Also provided are apparatus for texture mapping the specific 2-D slice image onto the planar surface of the second software object. Display apparatus are provided for displaying an image of the augmented 3-D computer model so as to simultaneously provide a view of the first software object and the specific 2-D slice image texture mapped onto the planar surface of the second software object.

16 Claims, 17 Drawing Sheets

U.S. PATENT DOCUMENTS

| | | | |
|---|---|---|---|
| 5,005,559 | 4/1991 | Blanco et al. | 128/4 |
| 5,151,856 | 9/1992 | Halmann et al. | 364/413.03 |
| 5,153,721 | 10/1992 | Eino et al. | 358/107 |
| 5,179,638 | 1/1993 | Dawson et al. | 395/125 |
| 5,230,623 | 7/1993 | Guthrie et al. | 433/72 |
| 5,231,483 | 7/1993 | Sieber et al. | 358/125 |
| 5,255,352 | 10/1993 | Falk | 395/125 |
| 5,261,404 | 11/1993 | Mick et al. | 128/653.1 |
| 5,274,551 | 12/1993 | Corby, Jr. | 364/413.13 |
| 5,291,889 | 3/1994 | Kenet et al. | 128/653.1 |
| 5,295,199 | 3/1994 | Shino | 382/41 |
| 5,297,215 | 3/1994 | Yamagishi | 382/6 |
| 5,319,551 | 6/1994 | Sekiguchi et al. | 364/413.19 |
| 5,329,310 | 7/1994 | Liljegren et al. | 348/147 |
| 5,363,476 | 11/1994 | Kurashige et al. | 395/125 |
| 5,378,915 | 1/1995 | Hines et al. | 250/369 |
| 5,383,454 | 1/1995 | Bucholz | 128/653.1 |
| 5,384,594 | 1/1995 | Sieber et al. | 348/169 |
| 5,398,684 | 3/1995 | Hardy | 128/653.1 |
| 5,417,210 | 5/1995 | Funda et al. | 128/653.1 |
| 5,447,154 | 9/1995 | Cinquin et al. | 128/653.1 |
| 5,448,687 | 9/1995 | Hoogerhyde et al. | 395/125 |
| 5,461,706 | 10/1995 | Trow et al. | 395/125 |
| 5,491,510 | 2/1996 | Gove | 348/77 |
| 5,493,595 | 2/1996 | Schoolman | 378/41 |
| 5,497,452 | 3/1996 | Shimizu et al. | 395/119 X |
| 5,511,153 | 4/1996 | Azarbayejani et al. | 395/119 |
| 5,526,812 | 6/1996 | Dumoulin et al. | 128/653.1 |
| 5,526,814 | 6/1996 | Cline et al. | 128/653.2 |
| 5,531,227 | 7/1996 | Schneider | 128/653.1 |
| 5,537,638 | 7/1996 | Morita et al. | 395/125 |
| 5,558,619 | 9/1996 | Kami et al. | 600/146 |

ANATOMICAL VISUALIZATION SYSTEM

FIELD OF THE INVENTION

This invention relates to medical apparatus in general, and more particularly to anatomical visualization systems.

BACKGROUND OF THE INVENTION

Many medical procedures must be carried out at an interior anatomical site which is normally hidden from the view of the physician. In these situations, the physician typically uses some sort of scanning device to examine the patient's anatomy at the interior site prior to, and in preparation for, conducting the actual medical procedure. Such scanning devices typically include CT scanners, MRI devices, X-ray machines, ultrasound devices and the like, and essentially serve to provide the physician with some sort of visualization of the patient's interior anatomical structure prior to commencing the actual medical procedure. The physician can then use this information to plan the medical procedure in advance, taking into account patient-specific anatomical structure. In addition, the physician can also use the information obtained from such preliminary scanning to more precisely identify the location of selected structures (e.g., tumors and the like) which may themselves be located within the interior of internal organs or other internal body structures. As a result, the physician can more easily "zero in" on such selected structures during the subsequent medical procedure. Furthermore, in many cases, the anatomical structures of interest to the physician may be quite small and/or difficult to identify with the naked eye. In these situations, preliminary scanning of the patient's interior anatomical structure using high resolution scanning devices can help the physician locate the structures of interest during the subsequent medical procedure.

In addition to the foregoing, scanning devices of the sort described above are frequently also used in purely diagnostic procedures.

In general, scanning devices of the sort described above tend to generate two-dimensional (i.e., "2-D") images of the patient's anatomical structure. In many cases, the scanning devices are adapted to provide a set of 2-D images, with each 2-D image in the set being related to every other 2-D image in the set according to some pre-determined relationship. For example, CT scanners typically generate a series of 2-D images, with each 2-D image corresponding to a specific plane or "slice" taken through the patient's anatomical structure. Furthermore, with many scanning devices, the angle and spacing between adjacent image planes or slices is very well defined, e.g., each image plane or slice may be set parallel to every other image plane or slice, and adjacent image planes or slices may be spaced a pre-determined distance apart. By way of example, the parallel image planes might be set 1 mm apart.

In a system of the sort just described, the physician can view each 2-D image individually and, by viewing a series of 2-D images in proper sequence, can mentally generate a three-dimensional (i.e., "3-D") impression of the patient's interior anatomical structure.

Some scanning devices include, as part of their basic system, associated computer hardware and software for building a 3-D database of the patient's scanned anatomical structure using a plurality of the aforementioned 2-D images. For example, some CT and MRI scanners include such associated computer hardware and software as part of their basic system. Alternatively, such associated computer hardware and software may be provided independently of the scanning devices, as a sort of "add-on" to the system; in this case, the data from the scanned 2-D images is fed from the scanning device to the associated computer hardware and software in a separate step. In either case, a trained operator using the scanning device can create a set of scanned 2-D images, assemble the data from these scanned 2-D images into a 3-D database of the scanned anatomical structure, and then generate various additional images of the scanned anatomical structure using the 3-D database. This feature is a very powerful tool, since it essentially permits a physician to view the patient's scanned anatomical structure from a wide variety of different viewing positions. As a result, the physician's understanding of the patient's scanned anatomical structure is generally greatly enhanced.

While the 2-D slice images generated by the aforementioned scanning devices, and/or the 3-D database images generated by the aforementioned associated computer hardware and software, are generally of great benefit to physicians, certain significant limitations still exist.

For one thing, with current systems, each scanned 2-D slice image is displayed as a separate and distinct image, and each image generated from the 3-D database is displayed as a separate and distinct image. Unfortunately, physicians can sometimes have difficulty correlating what they see on a particular scanned 2-D slice image with what they see on a particular image generated from the 3-D database.

OBJECTS OF THE PRESENT INVENTION

Accordingly, one object of the present invention is to provide an improved anatomical visualization system wherein a scanned 2-D slice image can be appropriately combined with an image generated from a 3-D database so as to create a single composite image.

Another object of the present invention is to provide an improved anatomical visualization system wherein a marker can be placed onto a 2-D slice image displayed on a screen, and this marker will be automatically incorporated, as appropriate, into a 3-D computer model maintained by the system, as well as into any other 2-D slice image data maintained by the system.

Still another object of the present invention is to provide an improved anatomical visualization system wherein a margin of pre-determined size can be associated with a marker of the sort described above, and further wherein the margin will be automatically incorporated into the 3-D computer model, and into any other 2-D slice image data, in association with that marker.

Yet another object of the present invention is to provide an improved anatomical visualization system wherein the periphery of objects contained in a 3-D computer model maintained by the system can be automatically identified in any 2-D slice image data maintained by the system, wherein the periphery of such objects can be highlighted as appropriate in 2-D slice images displayed by the system.

And another object of the present invention is to provide an improved method for visualizing anatomical structure.

SUMMARY OF THE INVENTION

These and other objects are addressed by the present invention, which comprises a visualization system comprising a first database that comprises a plurality of 2-D slice images generated by scanning a structure. The 2-D slice images are stored in a first data format. A second database is also provided that comprises a 3-D computer model of the scanned structure. The 3-D computer model comprises a first software object that is defined by a 3-D geometry database. Means are provided for inserting a second software object into the 3-D computer model so as to augment the 3-D computer model. The second software object is also defined by a 3-D geometry database, and includes a planar surface. Means for determining the specific 2-D slice image associated with the position of the planar surface of the second software object within the augmented 3-D computer model are provided in a preferred embodiment of the invention. Means are also provided for texture mapping the specific 2-D slice image onto the planar surface of the second software object. Display means are provided for displaying an image of the augmented 3-D computer model so as to simultaneously provide a view of the first software object and the specific 2-D slice image texture mapped onto the planar surface of the second software object.

In one alternative embodiment of the present invention, a visualization system is provided comprising a first database comprising a plurality of 2-D slice images generated by scanning a structure. The 2-D slice images are again stored in a first data format. A second database comprising a 3-D computer model of the scanned structure is also provided in which the 3-D computer model comprises a first software object that is defined by a 3-D geometry database. Means are provided for selecting a particular 2-D slice image from the first database. Means are also provided for inserting a second software object into the 3-D computer model so as to augment the 3-D computer model. The second software object is defined by a 3-D geometry database, and also includes a planar surface. In this alternative embodiment however, the second software object is inserted into the 3-D computer model at the position corresponding to the position of the selected 2-D slice image relative to the scanned structure. Means for texture mapping the specific 2-D slice image onto the planar surface of the second software object are also provided. Means are provided for displaying an image of the augmented 3-D computer model so as to simultaneously provide a view of the first software object and the specific 2-D slice image texture mapped onto the planar surface of the second software object.

In each of the embodiments of the present invention, the 3-D geometry database may comprise a surface model. Likewise, the system may further comprise means for inserting a marker into the first database, whereby the marker will be automatically incorporated into the second database, and further wherein the marker will be automatically displayed where appropriate in any image displayed by the system. Also, the system may further comprise a margin of pre-determined size associated with the marker. Additionally, the system may further comprise means for automatically determining the periphery of any objects contained in the second database and for identifying the corresponding data points in the first database, whereby the periphery of such objects can be highlighted as appropriate in any image displayed by the system. Often, the scanned structure will comprise an anatomical structure.

The present invention also comprises a method for visualizing an anatomical structure.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein.

DETAILED DESCRIPTION OF THE PREFERRED EMBODIMENT

Figure 1:
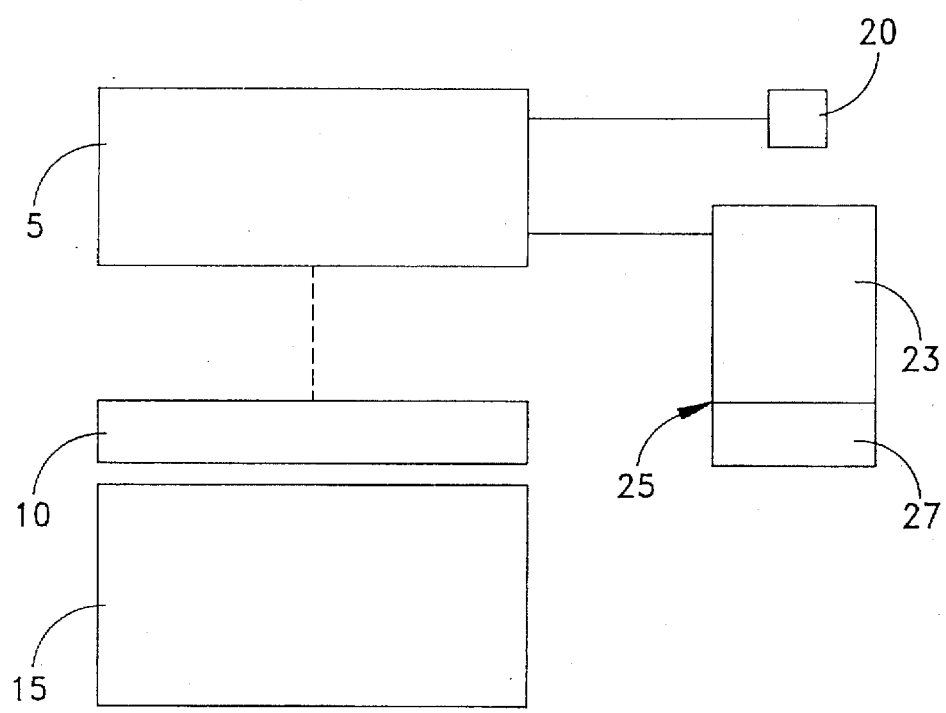
FIG. 1 is a schematic view showing a scanning device generating a set of 2-D images of the anatomy of a patient.

Looking first at FIG. 1, a scanning device 5 is shown as it scans the interior anatomical structure of a patient 10, as that patient 10 lies on a scanning platform 15.

Scanning device 5 is of the sort adapted to generate scanning data corresponding to a series of 2-D images, where each 2-D image corresponds to a specific viewing plane or "slice" taken through the patient's body. Furthermore, scanning device 5 is adapted so that the angle and spacing between adjacent image planes or slices can be very well defined, e.g., each image plane or slice may be set parallel to every other image plane or slice, and adjacent image planes or slices may be spaced a pre-determined distance apart. By way of example, the parallel image planes might be set 1 mm apart.

The scanning data obtained by scanning device 5 can be displayed as a 2-D slice image on a display 20, and/or it can be stored in its 2-D slice image data form in a first section 23 of a data storage device or medium 25. Furthermore, additional information associated with the scanning data (e.g. patient name, age, etc.) can be stored in a second section 27 of data storage device or medium 25.

By way of example, scanning device 5 might comprise a CT scanner of the sort manufactured by GE Medical Systems of Milwaukee, Wis.

Figure 2:
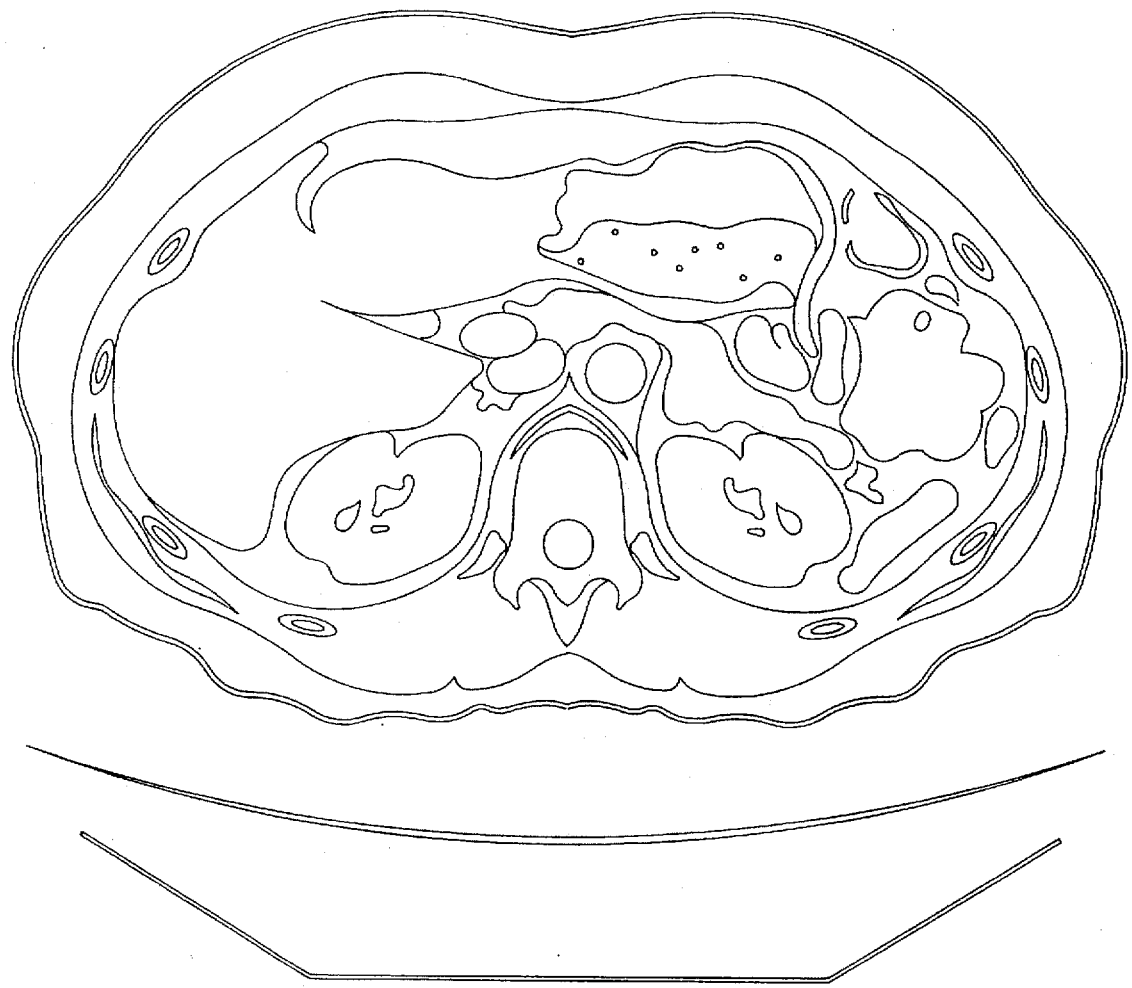
FIG. 2 is a 2-D slice image corresponding to an axial slice taken through the abdomen of an individual.

By way of further example, a 2-D slice image of the sort generated by scanning device 5 and displayed on display 20 might comprise the 2-D slice image shown in FIG. 2. In the particular example shown in FIG. 2, the 2-D slice image shown corresponds to an axial slice taken through an individual's abdomen and showing, among other things, that individual's liver.

Scanning device 5 may format its scanning data in any one of a number of different data structures. By way of example, scanning device 5 might format its scanning data in the particular data format used by a CT scanner of the sort manufactured by GE Medical Systems of Milwaukee, Wis. More specifically, with such a scanning device, the scanning data is generally held as a series of data "frames", where each data frame corresponds to a particular 2-D slice image taken through the patient's body. Furthermore, within each data frame, the scanning data is generally organized so as to represent the scanned anatomical structure at a particular location within that 2-D slice image. Such a data structure is fairly common for scanning devices of the sort associated with the present invention. However, it should be appreciated that the present invention is not dependent on the particlar data format utilized by scanning device 5. For the purposes of the present invention, the scanning data provided by scanning device 5 can be formatted in almost any desired data structure, so long as that data structure is well defined, whereby the scanning data can be retrieved and utilized as will hereinafter be disclosed in further detail.

Figure 3:
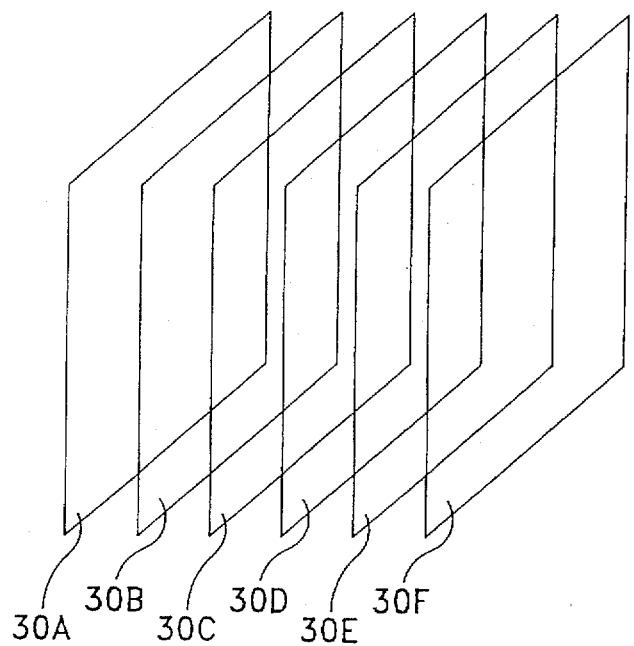
FIG. 3 shows a series of data frames corresponding to 2-D slice images arranged in a parallel array.
Figure 4:
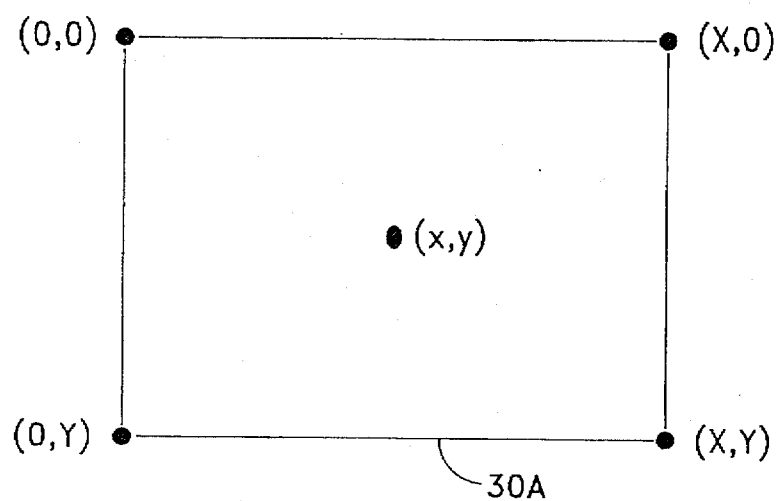
FIG. 4 is a schematic view showing the scanning data contained within an exemplary data frame.

For purposes of illustrating the present invention, it can be convenient to think of the scanning data generated by scanning device 5 as being organized in the data structures schematically illustrated in FIGS. 3 and 4.

More particularly, in FIG. 3, a series of data frames 30A, 30B, 30C, etc. are shown arranged in a parallel array. Each of these data frames 30A, 30B, 30C, etc. corresponds to a particular 2-D slice image taken through the patient's body by scanning device 5, where the 2-D slice images are taken parallel to one another. In addition, adjacent image planes or slices are spaced apart by a constant, predetermined distance, e.g., 1 mm.

Furthermore, in FIG. 4, the scanning data contained within an exemplary data frame 30A is shown represented in an X-Y coordinate scheme so as to quickly and easily identify the scanned anatomical structure disposed at a particular location within that 2-D slice image. Typically, the scanning data relating to a particular X-Y coordinate represents an image intensity value. This image intensity value generally reflects some attribute of the specific anatomical structure being scanned, e.g., the tissue density.

As noted above, the scanning data generated by scanning device 5 is stored in its 2-D slice image data form in first section 23 of data storage device or medium 25, with the scanning data being stored in a particular data format as determined by the manufacturer of scanning device 5.

Figure 5:
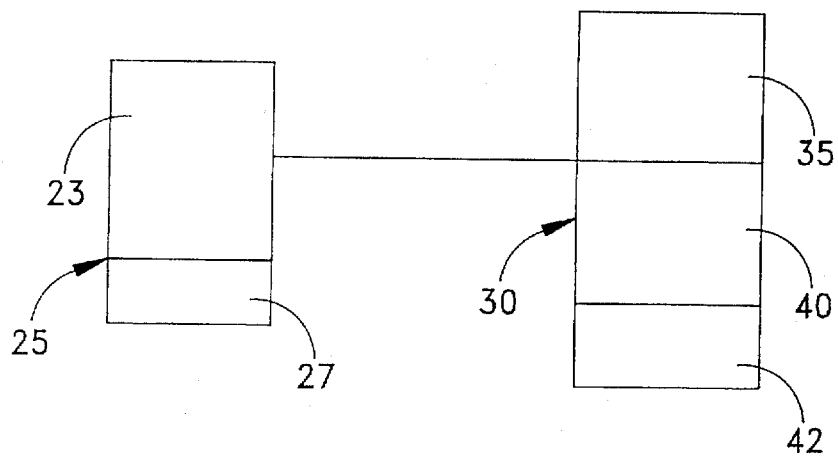
FIG. 5 shows scanning data stored in a first storage device or medium being retrieved, processed and then stored again in a second data storage device or medium.

In accordance with the present invention, and looking now at FIG. 5, the scanning data stored in first section 23 of data storage device or medium 25 is retrieved, processed and then stored again in a data storage device or medium 30.

More particularly, the scanning data stored in first section 23 of data storage device or medium 25 is retrieved and processed so as to convert the scanning data generated by scanning device 5 from its 2-D slice image data form into a 3-D computer model of the patient's anatomical structure. This 3-D computer model is then stored in a first section 35 of data storage device or medium 30.

In addition, the scanning data stored in first section 23 of data storage device or medium 25 is retrieved and processed as necessary so as to convert the scanning data into a preferred data format for the 2-D slice image data. The 2-D slice image data is then stored in this preferred data format in second section 40 of data storage device or medium 30.

Furthermore, the additional information associated with the scanning data (e.g. patient name, age, etc.) which was previously stored in second section 27 of data storage device or medium 25 can be stored in a third section 42 of data storage device or medium 30.

In accordance with the present invention, once the 3-D computer model has been stored in first section 35 of data storage device or medium 30, and the 2-D slice image data has been stored in a preferred data format in second section 40 of data storage device or medium 30, a physician can then use an appropriately programmed computer to access the 3-D computer model stored in first section 35 of data storage device or medium 30, and/or the 2-D slice image data stored in second section 40 of data storage device or medium 30, to generate desired patient-specific images.

Figure 6:
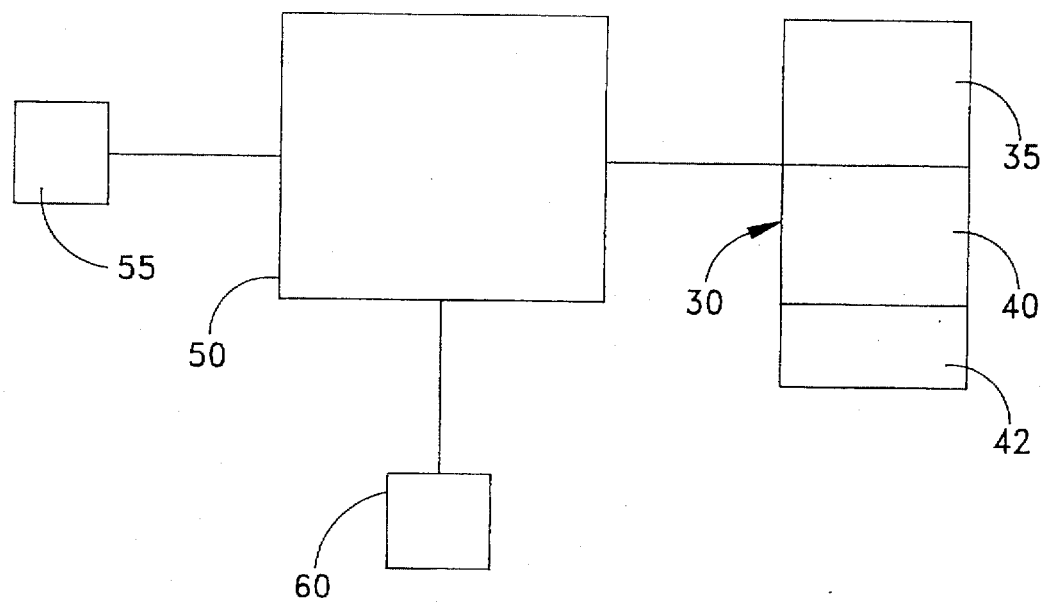
FIG. 6 is a schematic view of a system for retrieving and viewing scanning data.

More particularly, and looking now at FIG. 6, once the 3-D computer model has been stored in first section 35 of data storage device or medium 30, and the 2-D slice image data has been stored in a preferred data format in second section 40 of data storage device or medium 30, a physician can use an appropriately programmed computer 50, operated by input devices 55, to access the 3-D computer model stored in first section 35 of data storage device or medium 30, and/or the 2-D slice image data stored in second section 40 of data storage device or medium 30, so as to generate the desired patient-specific images and display those images on a display 60.

To this end, it will be appreciated that the specific data structure used to store the 3-D computer model in first section 35 of data storage device or medium 30, and the specific data structure used to store the 2-D slice image data in second section 40 of data storage device or medium 30, will depend on the specific nature of computer 50 and on the particular operating system and application software being run on computer 50.

Figure 7:
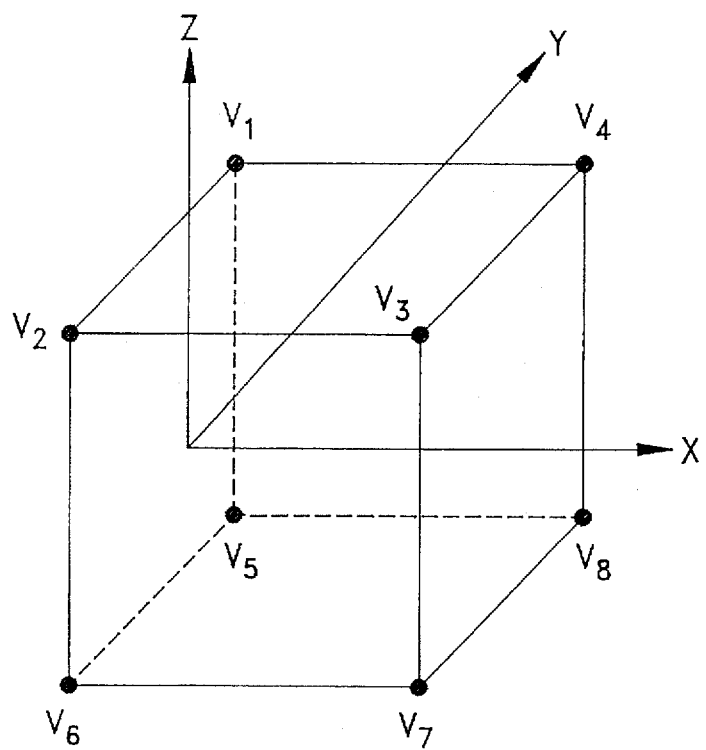
FIG. 7 is a schematic view of a unit cube for use in defining polygonal surface models.
Figure 8:
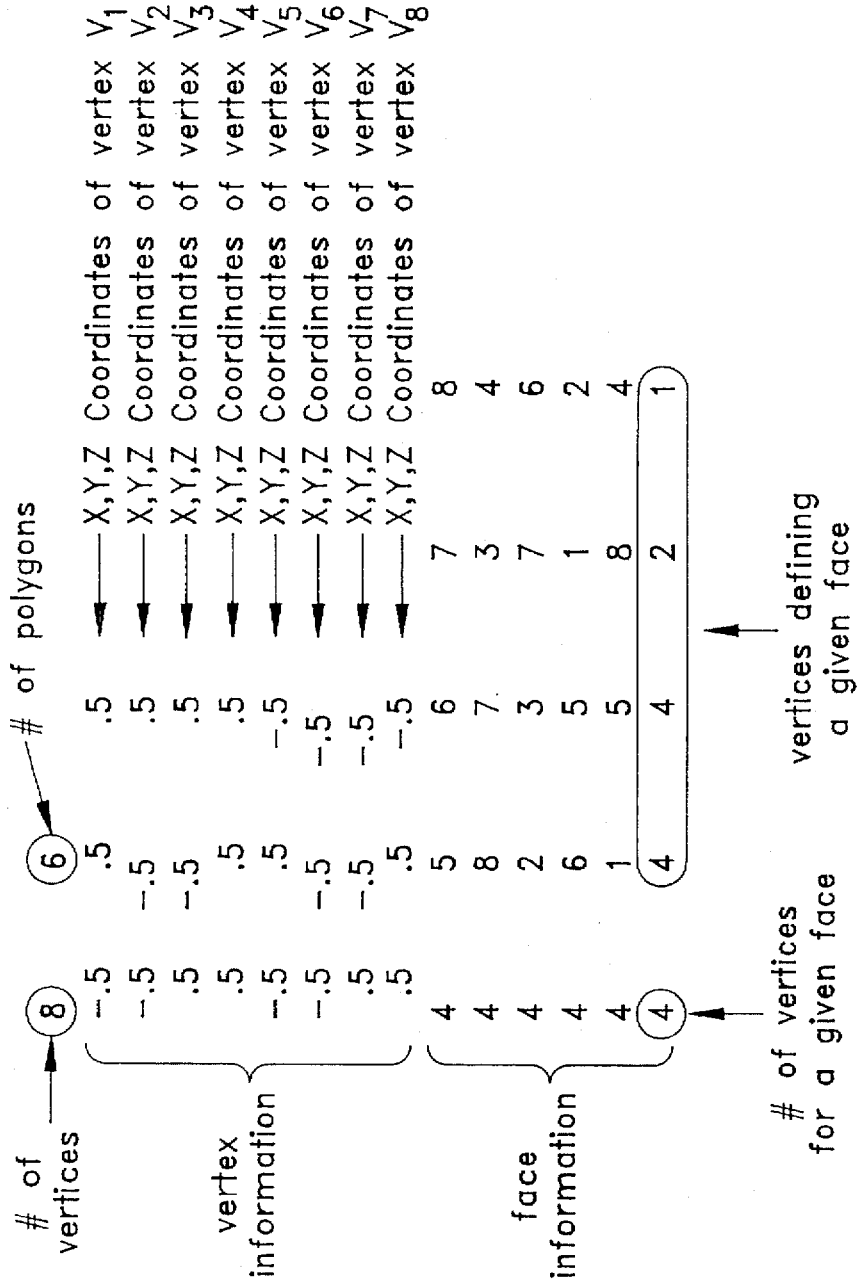
FIG. 8 illustrates the data file format of the polygonal surface model for the simple unit cube shown in FIG. 7.
Figure 9A:
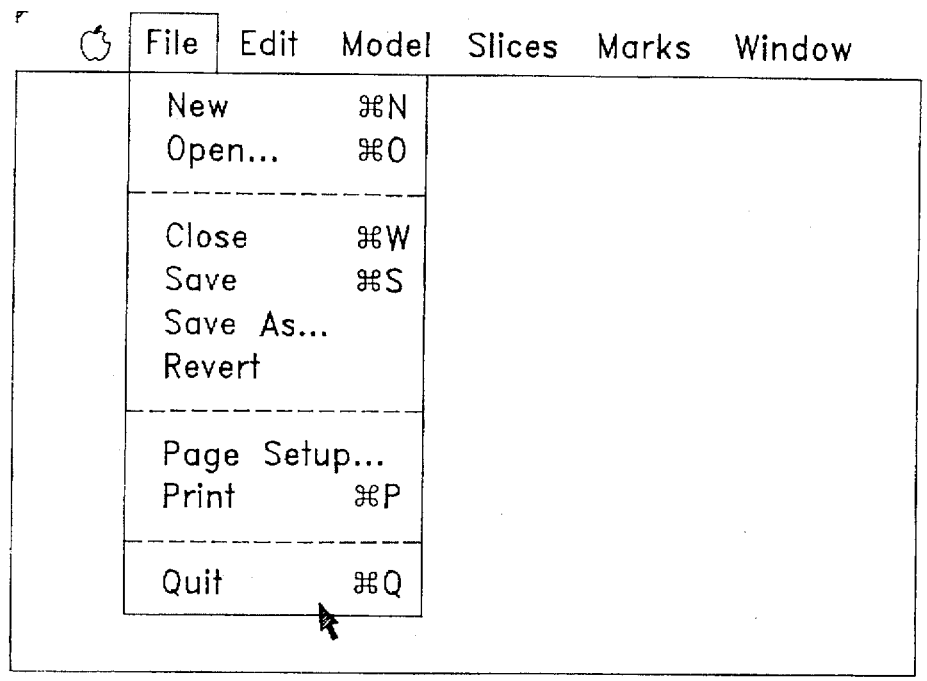
FIGS. 9A–9F illustrate a variety of menu choices which may be utilized in connection with the present invention.
Figure 9B:
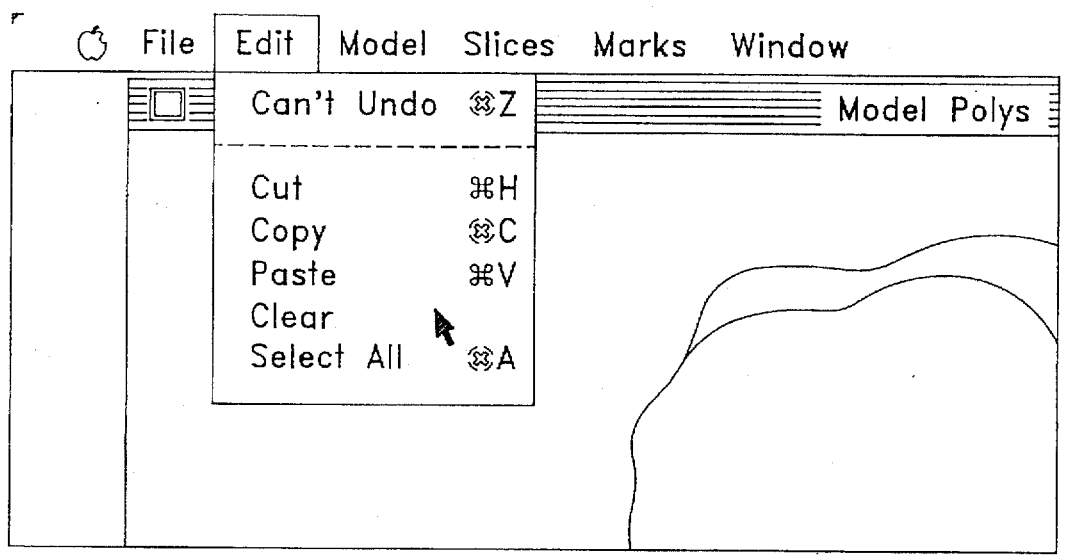
Figure 9C:
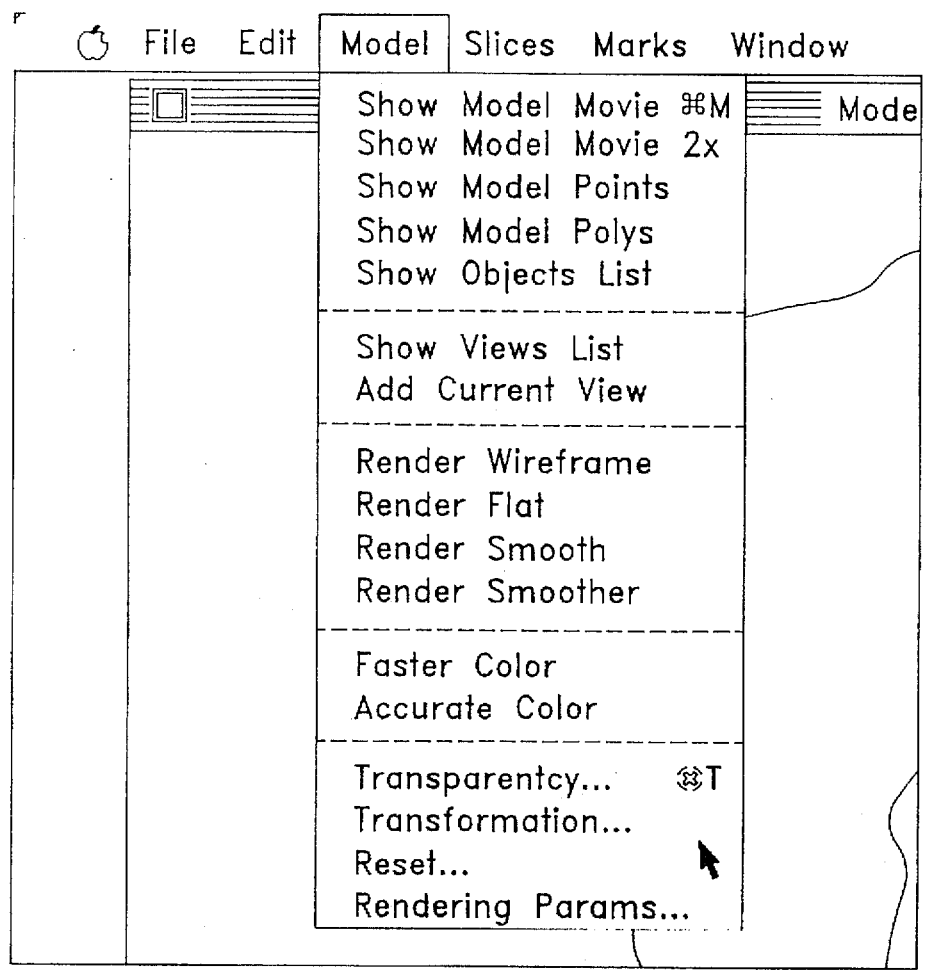
Figure 9D:
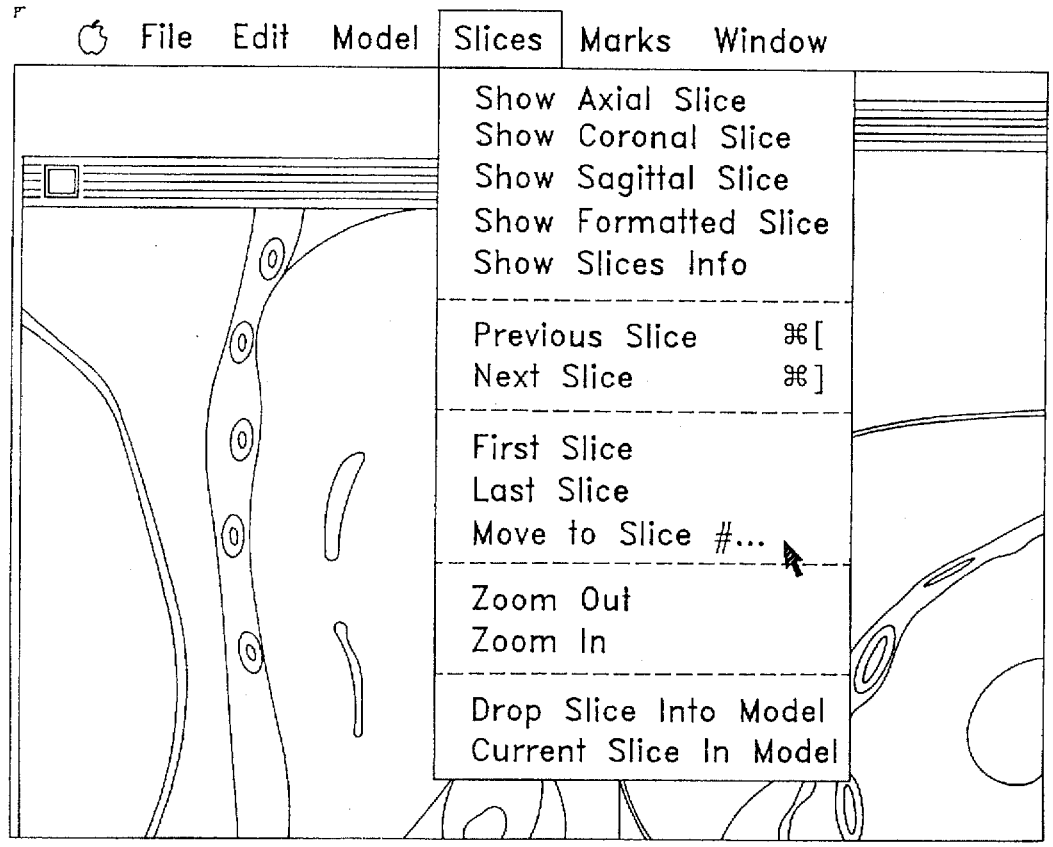
Figure 9E:
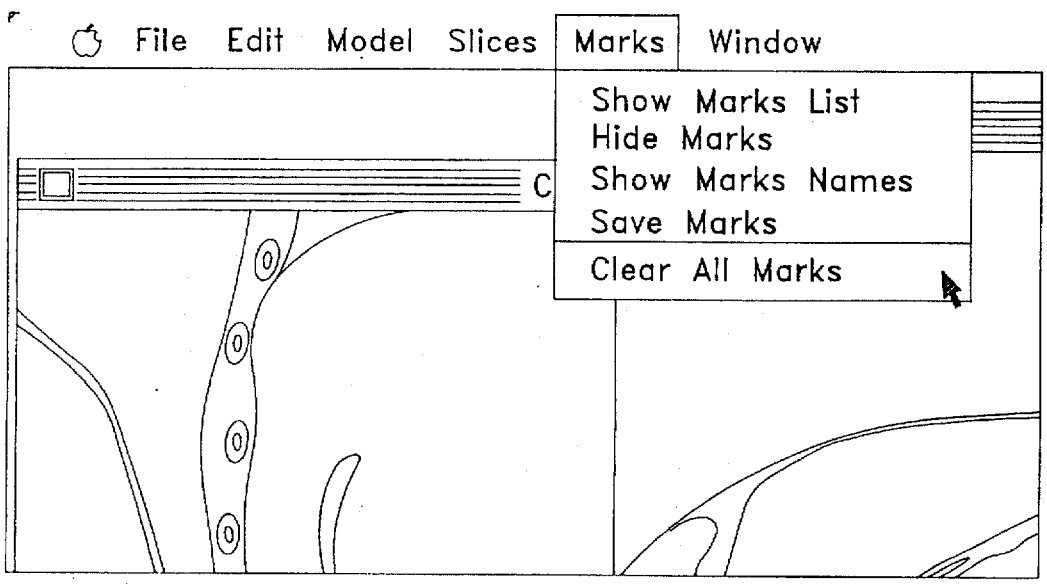
Figure 9F:
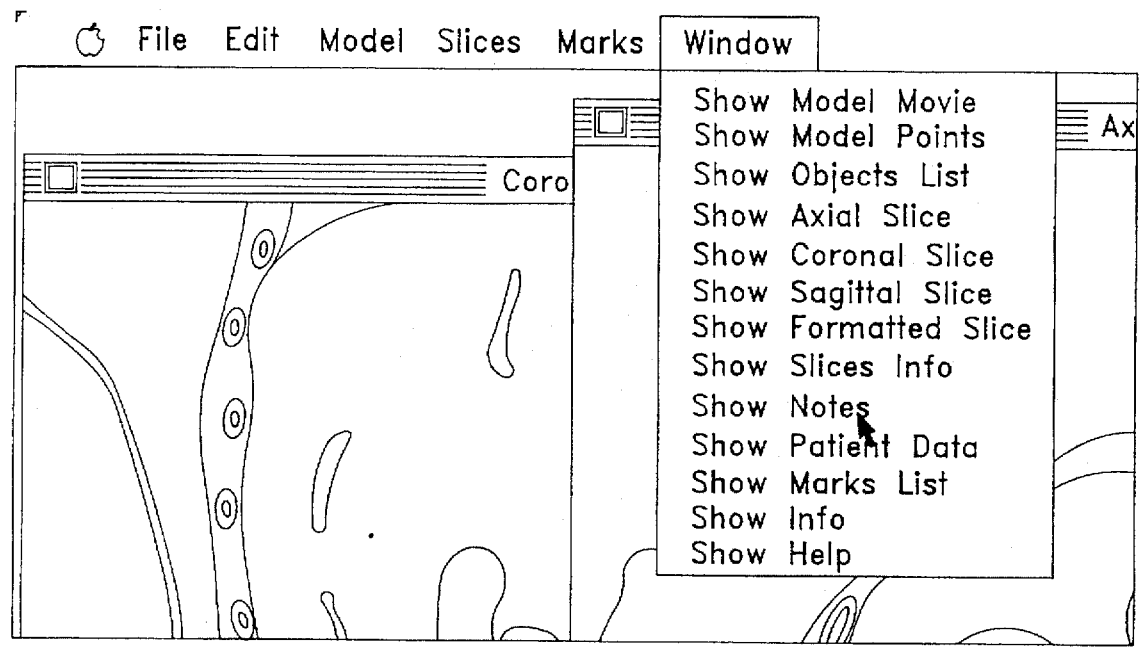

In general, however, the 3-D computer model contained in first section 35 of data storage device or medium 30 is preferably structured as a collection of software objects, with each software object being defined by a polygonal surface model of the sort well known in the art. By way of example, a scanned anatomical structure such as a human liver might be modeled as three distinct software objects, with the outer surface of the general mass of the liver being one software object, the outer surface of the vascular structure of the liver being a second software object, and the outer surface of a tumor located in the liver being a third software object. By way of further example, FIGS. 7 and 8 illustrate a typical manner of defining a software object by a polygonal surface model. In particular, FIG. 7 illustrates the vertices of a unit cube set in an X-Y-Z coordinate system, and FIG. 8 illustrates the data file format of the polygonal surface model for this simple unit cube. As is well known in the art, more complex shapes such as human anatomical structure can be expressed in corresponding terms.

Furthermore, the 3-D computer model contained in first section 35 of data storage device or medium 30 is created by analyzing the 2-D slice image data stored in first section 23 of data storage device or medium 25 using techniques well known in the art. For example, the 2-D slice image data stored in first section 23 of data storage device or medium 25 might be processed using the well known "Marching Cubes" algorithm, which is a so-called "brute force" surface construction algorithm that extracts isodensity surfaces from volume data, producing from one to five triangles within voxels that contain the surface. Alternatively, the 2-D slice image data stored in first section 23 of data storage device or medium 25 might be processed into the 3-D computer model stored in first section 35 of data storage device or medium 30 by some other appropriate modelling algorithm so as to yield the desired 3-D computer model.

As noted above, the specific data structure used to store the 2-D slice image data in second section 40 of data storage device or medium 30 will also depend on the specific nature of computer 50 and on the particular operating system and application software being run on computer 50.

In general, however, the 2-D slice image data contained in second section 40 of data storage device or medium 30 is preferably structured as a series of data "frames", where each data frame corresponds to a particular 2-D slice image taken through the patient's body, and where the scanning data within each data frame is organized so as to represent the scanned anatomical structure at a particular location within that 2-D slice image.

In the present invention, it is preferred that computer 50 comprise a Power PC-based, Macintosh operating system ("Mac OS") type of computer, e.g. a Power PC Macintosh 8100/80 of the sort manufactured by Apple Computer, Inc. of Cupertino, Calif. In addition, it is preferred that computer 50 be running Macintosh operating system software, e.g. Mac OS Ver. 7.5.1, such that computer 50 can readily access a 3-D computer model formatted in Apple's well-known QuickDraw 3D data format and display images generated from that 3D computer model, and such that computer 50 can readily access and display 2-D images formatted in Apple's well-known QuickTime image data format. Input devices 55 preferably comprise the usual computer input devices associated with a Power PC-based, Macintosh operating system computer, e.g., input devices 55 preferably comprise a keyboard, a mouse, etc.

In view of the foregoing, in the present invention it is also preferred that the 3-D computer model contained in first section 35 of data storage device or medium 30 be formatted in Apple's QuickDraw 3D data format, whereby the Mac OS computer 50 can quickly and easily access the 3-D computer model contained in first section 35 of data storage device or medium 30 and display images generated from that 3-D computer model on display 60.

In view of the foregoing, in the present invention it is also preferred that the 2-D slice image data contained in second section 40 of data storage device or medium 30 be formatted in Apple's QuickTime image data format. In this way computer 50 can quickly and easily display the scanned 2-D slice images obtained by scanning device 5. It will be appreciated that, to the extent that scanning device 5 happens to format its scanning data in the preferred QuickTime image data format, no reformatting of the 2-D slice image data will be necessary prior to storing the 2-D slice image data in second section 40 of data storage device or medium 30. However, to the extent that scanning device 5 happens to format its scanning data in a different data structure, reformatting of the 2-D slice image data will be necessary so as to put it into the preferred QuickTime image data format. Such image data reformatting is of the sort well known in the art.

As a result of the foregoing, it will be seen that a physician operating computer 50 through input devices 55 can generate a desired image from the 3-D computer model contained within first section 35 of data storage device or medium 30.

In particular, the physician can use input devices 55 to (1) open a window on display 60, (2) instruct the computer as to the desired angle of view, (3) generate the corresponding image of the scanned anatomical structure from the desired angle of view, using the 3-D computer model contained within first section 35 of data storage device or medium 30, and (4) display that image in the open window on display 60.

In addition, a physician operating computer 50 through input devices 55 can display a desired 2-D slice image from the 2-D slice image data contained within second section 40 of data storage device or medium 30. In particular, the physician can use input devices 55 to (1) open a window on display 60, (2) select a particular 2-D slice image contained within second section 40 of data storage device or medium 30, and (3) display that slice image in the open window on display 60.

More particularly, and looking now at FIGS. 9A–9F, computer 50 is preferably programmed so as to provide a variety of pre-determined menu choices which may be selected by the physician operating computer 50 via input devices 55.

Figure 10:
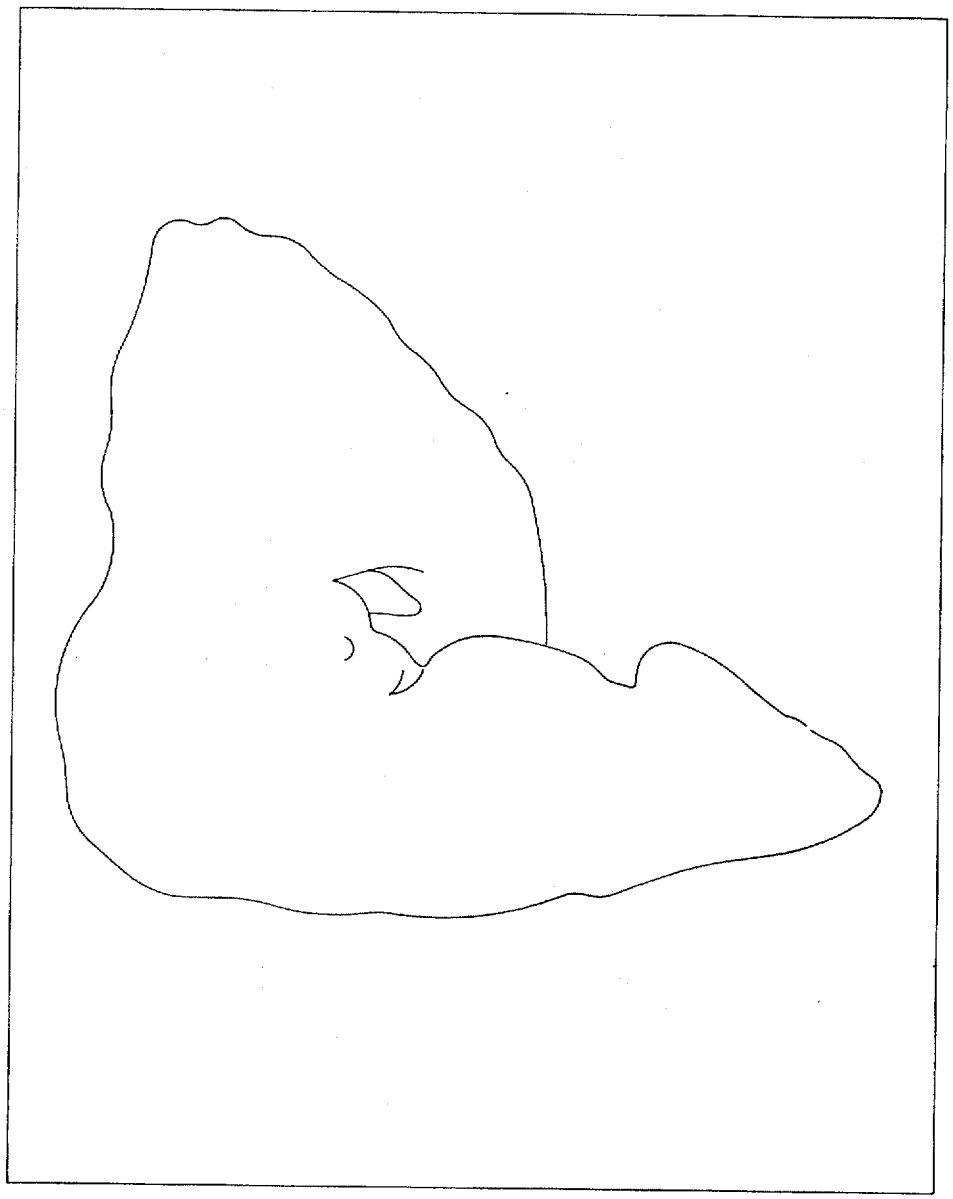
FIG. 10 illustrates an image drawn to a window using the data contained in the 3-D computer model associated with the present invention.

Thus, for example, if the physician wishes to produce a desired image from the 3-D computer model contained within first section 35 of data storage device or medium 30, the physician uses input devices 55 to invoke the command to display the 3-D computer model; the software then creates a window to display the image, it renders an image from the 3-D computer model contained within first section 35 of data storage device or medium 30, and then displays that image in the open window on display 60. By way of example, FIG. 10 illustrates an image drawn to a window using the data contained in the 3-D computer model stored in first section 35 of data storage device or medium 30. The physician can use input devices 55 to instruct the image rendering software as to the particular angle of view desired. In particular, the physician can depress a mouse key and then drag on the object so as to rotate the object into the desired angle of view. Additionally, one can also use the keyboard and mouse to move the view closer in or further out, or to translate the object side to side or up and down relative to the image plane. Programming to effect such computer operation is of the sort well known in the art.

Figure 11:
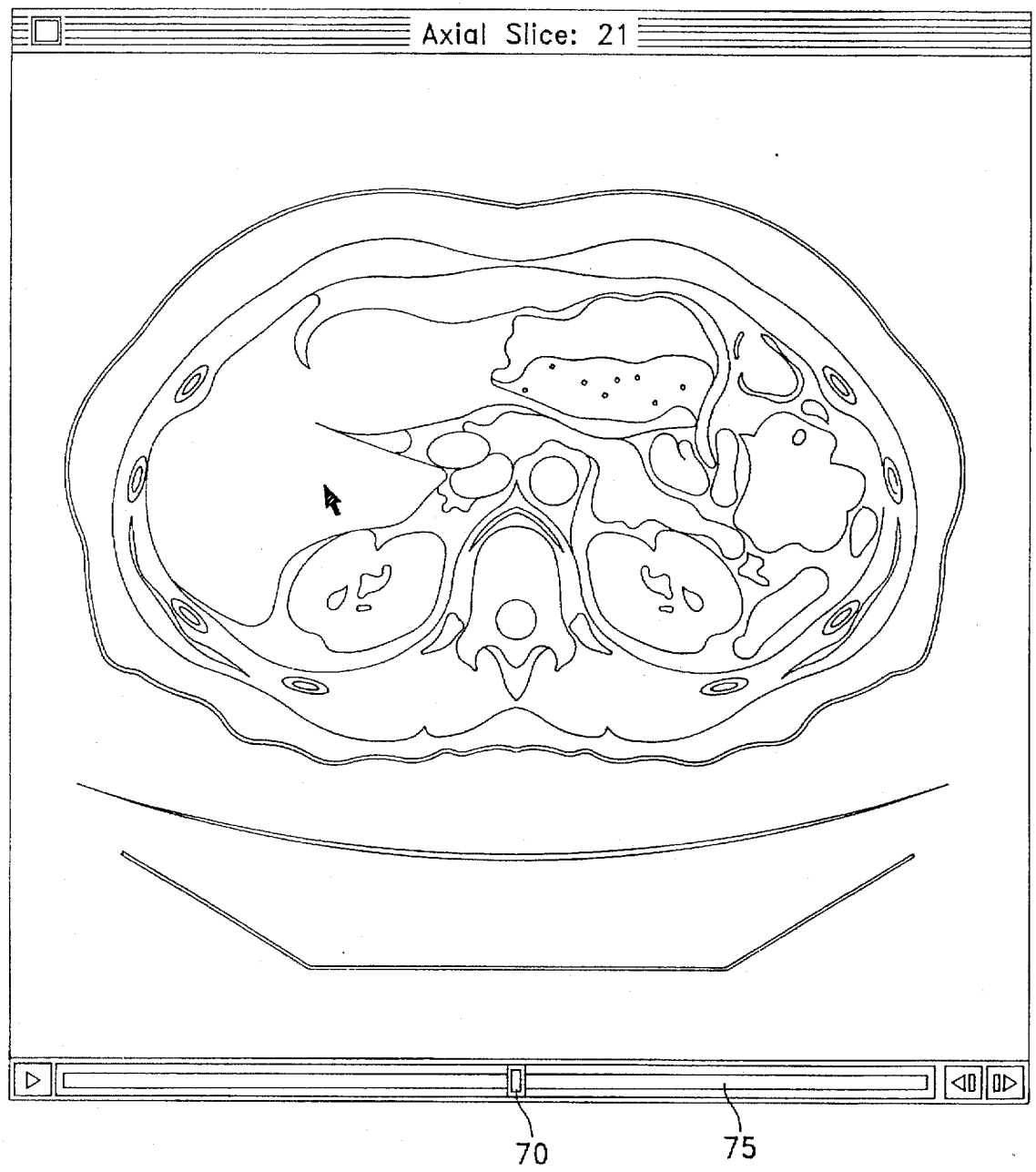
FIG. 11 illustrates a 2-D slice image drawn to a window in accordance with the present invention.

In a similar manner, the physician can use menu choices such as those shown in FIGS. 9A–9F to open a window on the display 60 to display a desired 2-D image slice from second section 40 of data storage device or medium 30 in that window. The physician can select between different image slices utilizing input devices 55. By way of example, FIG. 11 illustrates a 2-D image slice drawn to a window by the operating system using the data contained in second section 40 of data storage device or medium 30. By dragging icon 70 back and forth along slider 75, the physician can "leaf" back and forth through the collection of axial slices, i.e., in the example of FIG. 11 in which axial slice #21 is displayed, dragging icon 70 to the left might cause axial slice #20 to be displayed, and dragging icon 70 to the right might cause axial slice #22 to be displayed. Additionally, one can also step the image from the current slice number to a previous or following slice number, using menu commands or by clicking the mouse cursor on the single step icons set at the right side of slider 75. Menu commands can also be provided to change the slice window display directly to the first or last slice image in the 2-D slice image set, or to change the slice window display to a user-specified slice number. Programming to effect such computer operation is of the sort well known in the art.

Figure 12:
FIG. 12 illustrates a composite image formed from information contained in both the 3-D computer model and the 2-D image slice data structure.

As a consequence of using the aforementioned image rendering software, i.e., the Mac OS, the Apple QuickDraw 3D data format and software, and the Apple QuickTime image data format and software, or some equivalent hardware and software, it is possible to insert an additional software object into the 3-D computer model contained within first section 35 of data storage device or medium 30. In particular, it is possible to insert an additional software object having a "blank" planar surface into the 3-D computer model. Furthermore, using the computer's image rendering software, it is possible to texture map a 2-D slice image from second section 40 of data storage device or medium 30 onto the blank planar surface of the software object. Most significantly, since the 3-D computer model is created out of the same scanning data as the 2-D slice images, it is possible to determine the specific 2-D slice image associated with a given position of the blank planar surface. Accordingly, when an image is generated from the 3-D computer model, both 3-D model structure and 2-D image slice structure can be simultaneously displayed in proper registration with one another, thereby providing a single composite image of the two separate images. See, for example, FIG. 12, which shows such a composite image. Again, the physician can use input devices 55 to instruct the operating system's image rendering software as to where the aforementioned "additional" software object is to be inserted into the model and as to the particular angle of view desired. Programming to effect such computer operation is of the sort well known in the art.

In the foregoing description of the present invention, the 2-D slice image data generated by scanning device 5 has generally been discussed in the context of the standard "axial" slice images normally generated by scanning devices of the type associated with this invention. However, it is to be appreciated that it is also possible to practice the present invention in connection with sagittal or coronal 2-D slice images.

Figure 13:
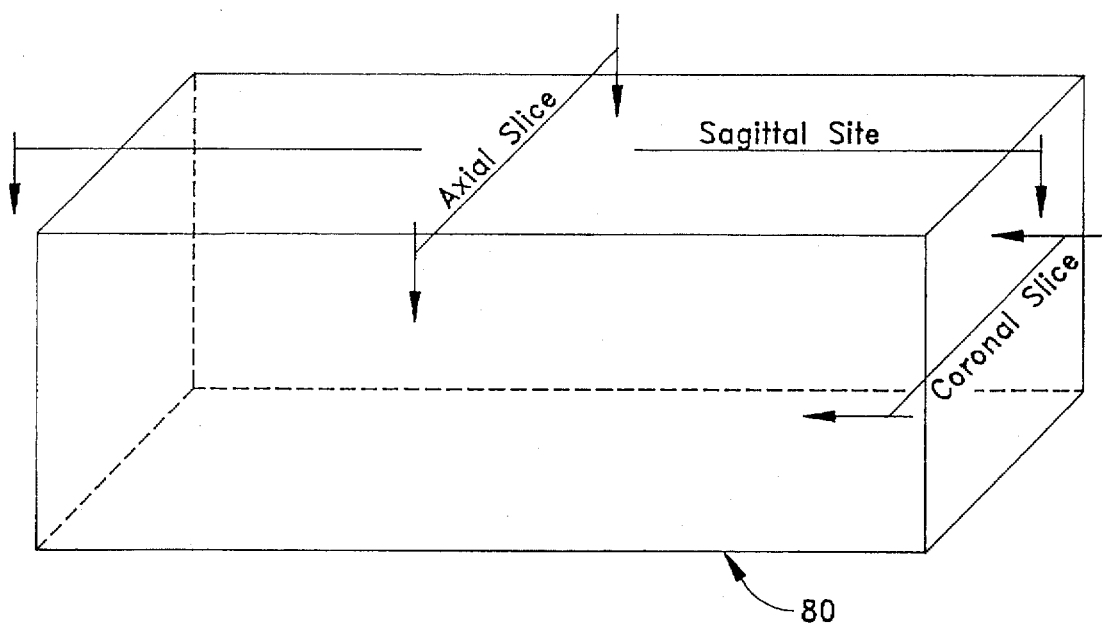
FIG. 13 is a schematic illustration showing the relationship between axial slices, sagittal slices and coronal slices.

More particularly, and looking next at FIG. 13, the relative orientation of axial, sagittal and coronal slice images are shown in the context of a schematic view of a human body 80. Scanning device 5 will normally generate axial slice image data when scanning a patent. In addition, in many cases scanning device 5 will also assemble the axial slice data into a 3-D database of the scanned anatomical structure, and then use this 3-D database to generate a corresponding set of sagittal and/or coronal 2-D slice images. In the event that scanning device 5 does not have the capability of generating the aforementioned sagittal and/or coronal 2-D slice images, these 2-D slice images may be generated from a set of the axial 2-D images in a subsequent operation, using computer hardware and software of the sort well known in the art. Alternatively, computer 50 could be programmed to render such sagittal and/or coronal 2-D slices "on the fly" from the 2-D slice image data contained in second section 40 of data storage device or medium 30.

Figure 14:
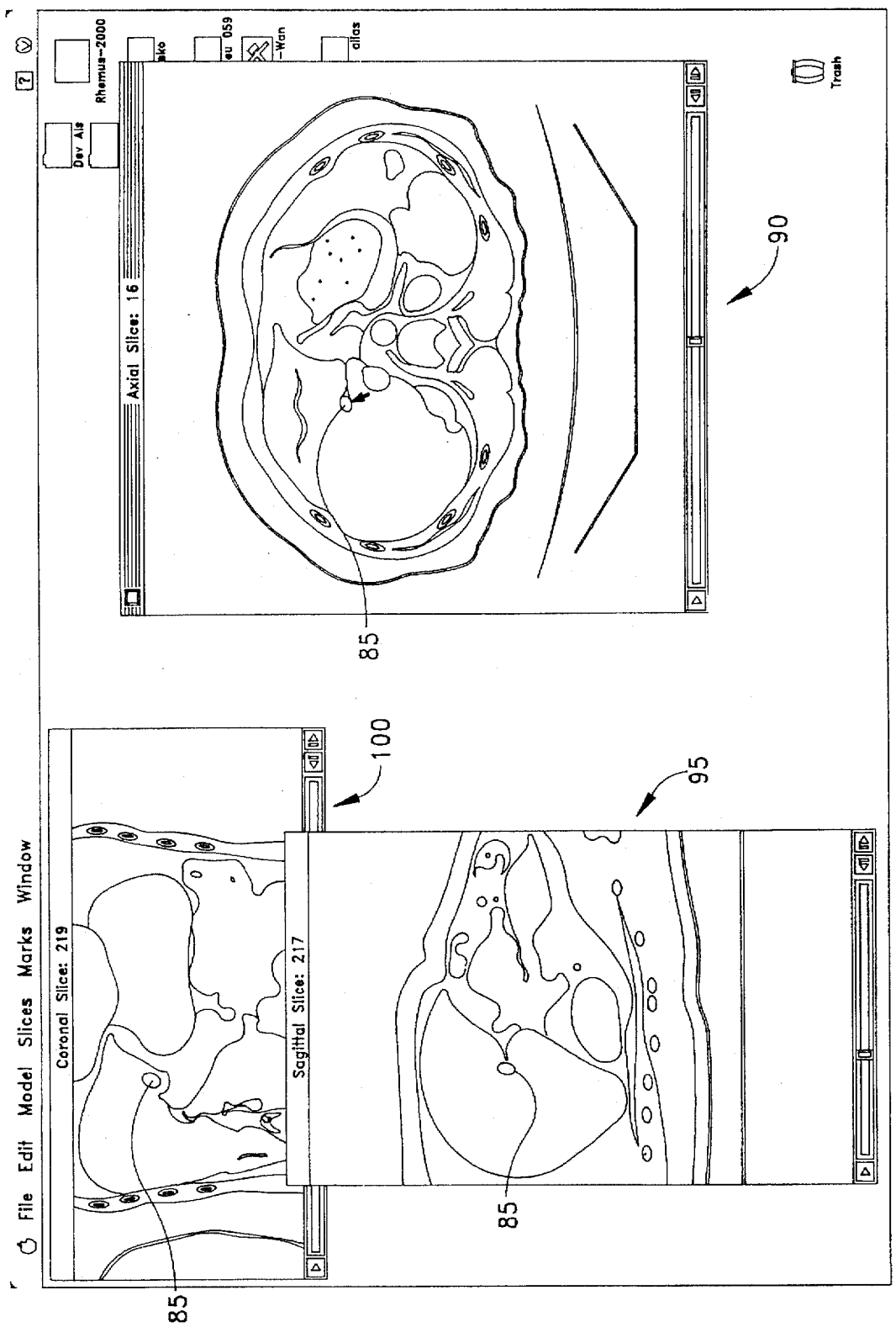
FIG. 14 illustrates three different 2-D slice images being displayed on a computer screen at the same time, with a marker being incorporated into each of the images.

In connection with the present invention, the sagittal and coronal 2-D slice image data may be stored with the axial slice image data in second section 40 of data storage device or medium 30. Preferably these sagittal and coronal slice images are stored in exactly the same data format as the 2-D axial slice images, whereby they may be easily accessed by computer 50 and displayed on display 60 in the same manner as has been previously discussed in connection with axial 2-D slice images. As a result, axial, sagittal and coronal 2-D slice images can be displayed on display 60, either individually or simultaneously in separate windows, in the manner shown in FIG. 14. Furthermore, when generating a composite image of the sort shown in FIG. 12 (i.e., an image generated from both the 3-D computer model contained in first section 35 of data storage device or medium 30 and a 2-D slice image contained in second section 40 of data storage device or medium 30), the composite image can be created using axial, sagittal or coronal 2-D slice images, as preferred.

It is also to be appreciated that the system of the present invention could be configured to generate and utilize oblique 2-D slice image date in place of the axial, sagittal and coronal slice image data described above.

In a further aspect of the present invention, it is possible to display a specific 2-D slice image in a window opened on display 60, place a marker into that specific 2-D slice image using a mouse or other input device 55, and then have that marker automatically incorporated into both (i) the 3-D computer model contained in first section 35 of data storage device or medium 30, and (ii) any appropriate 2-D slice image data contained in second section 40 of data storage device or medium 30. As a result, when images are thereafter generated from the 3-D computer model contained in first section 35 of data storage device or medium 30 and/or from the 2-D slice image data contained in second section 40 of data storage device or medium 30, these subsequent images will automatically display the marker where appropriate. See, for example, FIG. 14, which shows one such marker 85 displayed in its appropriate location in each of the three displayed 2-D slice images, i.e., in axial slice image 90, sagittal slice image 95, and coronal slice image 100. It is to be appreciated that it is also possible for a marker 85 to be displayed in an image generated from the 3-D computer model contained in first section 35 of data storage device or medium 30; see, for example, FIG. 15, which shows such a marker 85.

Figure 15:
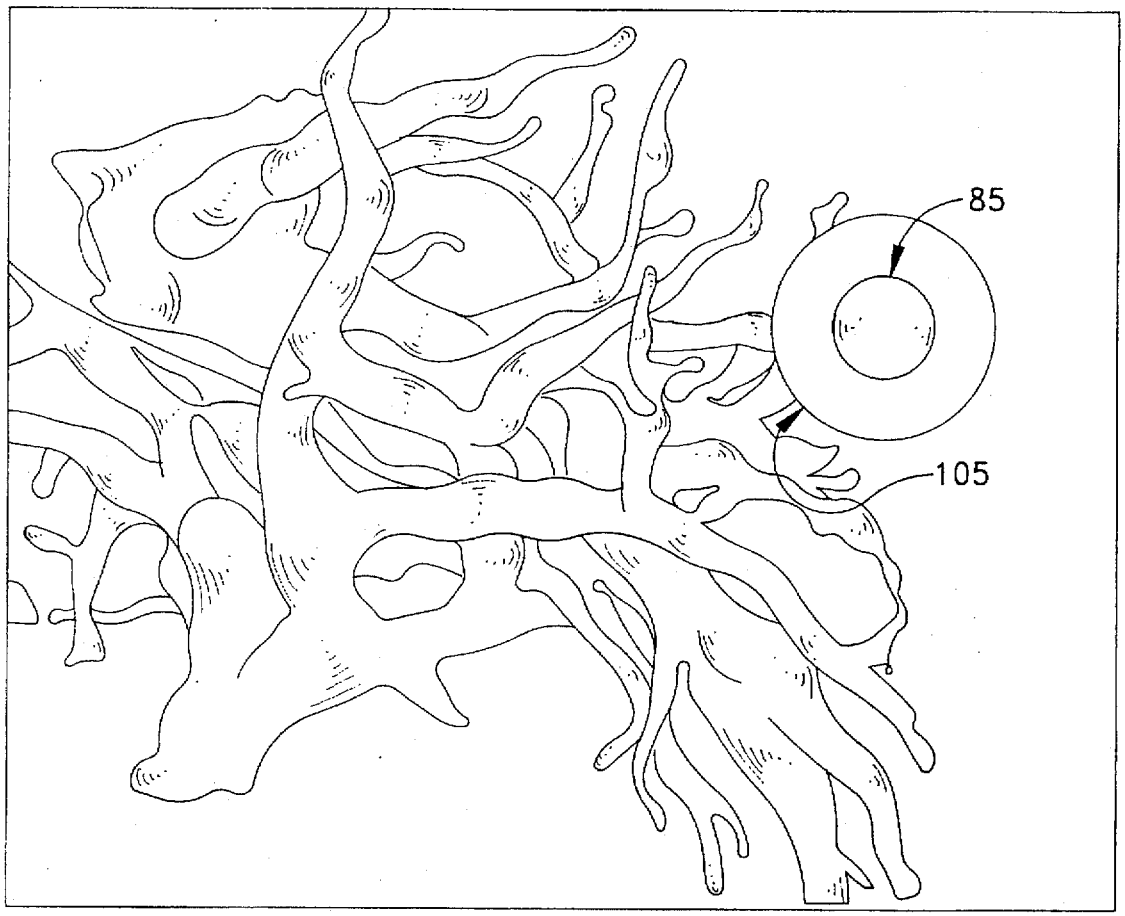
FIG. 15 illustrates a marker shown in an image generated from the 3-D computer model, with the marker being surrounded by a margin of pre-determined size.

In yet another aspect of the present invention, it is possible to generate a "margin" of some predetermined size around such a marker. Thus, for example, in FIG. 15, a margin 105 has been placed around marker 85. In this respect it is to be appreciated that margin 105 will appear as a 3-dimensional spherical shape around marker 85, just as marker 85 appears as a 3-dimensional shape, since the view of FIG. 15 is generated from the 3-D computer model contained in first section 35 of data storage device or medium 30. Alternatively, where marker 85 and margin 105 are displayed in the context of 2-D slice images, the marker and margin will appear as simple circles. Margin 105 can be used by a surgeon to determine certain spatial relationships in the context of the anatomical structure being displayed on the computer.

Figure 16:
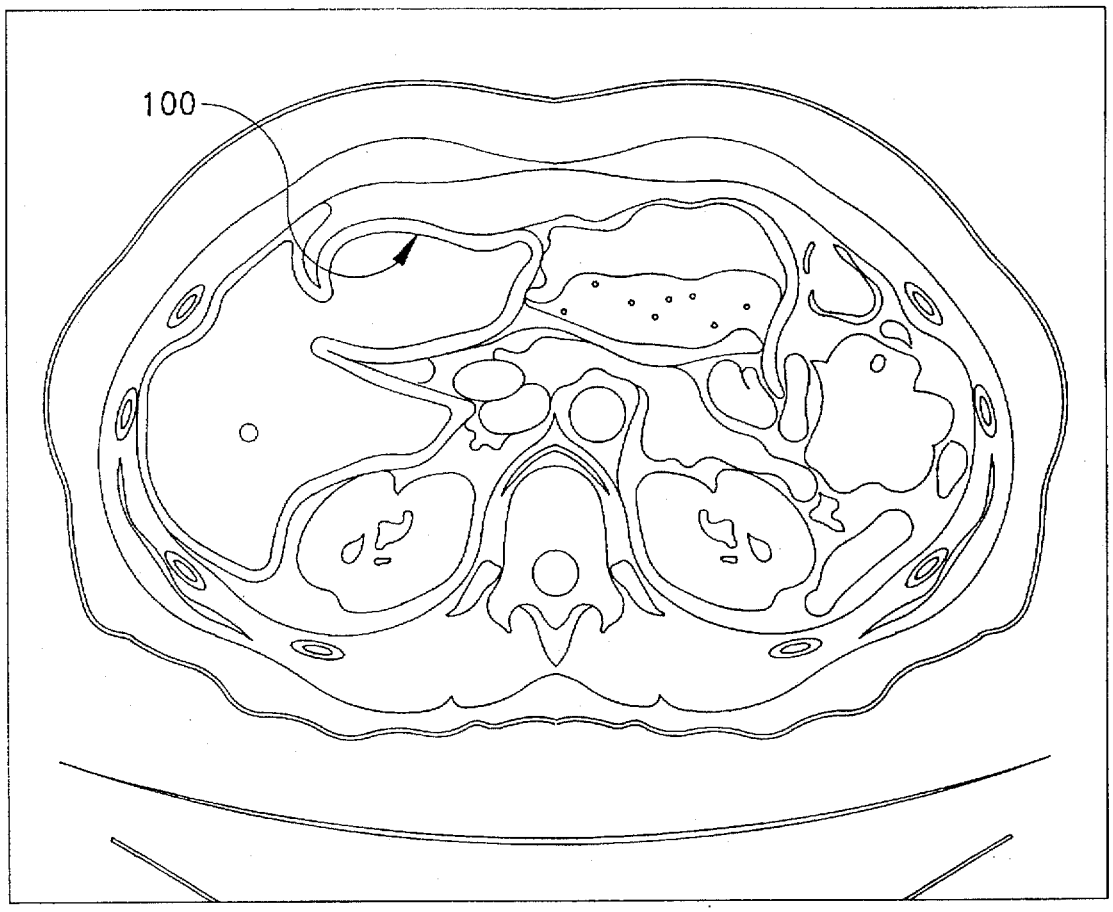
FIG. 16 illustrates a 2-D slice image, wherein the periphery of an object has been automatically highlighted by the system.

It is also to be appreciated that, inasmuch as the 3-D computer model contained in first section 35 of data storage device or medium 30 constitutes a plurality of software objects defined by polygonal surface models, it is possible to identify the periphery of any such objects in any corresponding 2-D slice image data contained in second section 40 of data storage device or medium 30. As a result, it is possible to highlight the periphery of any such object in any 2-D slice images displayed on display 60. Thus, for example, in FIG. 16, a boundary 110 is shown outlining the periphery of an object 115 displayed in a 2-D slice image.

Furthermore, while in the foregoing description the present invention has been described in the context of an anatomical visualization system, it is also to be appreciated that the system could be used in conjunction with inanimate objects, e.g., the system could be used to visualize substantially any object for which a 3-D computer model and a collection of 2-D slice image data can be assembled.

It is also anticipated that one might replace the polygonal surface model discussed above with some other type of surface model. Thus, as used herein, the term "surface model" is intended to include polygonal surface models, parametric surface models, such as B-spline surface models, quadralateral meshes, etc.

It is also to be understood that the present invention is by no means limited to the particular construction herein disclosed and/or shown in the drawings, but also comprises any modifications or equivalents within the scope of the claims.

What is claimed is:

1. A visualization system comprising:

a first database comprising a plurality of 2-D slice images generated by scanning a structure such that each of said 2-D slice images comprises a cross-sectional view of said structure as taken at a plane extending through said structure, said 2-D slice images being stored in a 2-D data format;

a second database comprising a 3-D computer model of said scanned structure, said 3-D computer model being generated from said 2-D slice images contained in said first database, said 3-D computer model comprising at least a first software object representative of at least a portion of said scanned structure, said first software object being defined by a 3-D geometry database;

means for generating a second software object and for inserting said second software object into said 3-D computer model such that said second software object co-exists with said first software object within said 3-D computer model so as to augment said 3-D computer model, said second software object being defined by a 3-D geometry database and including a planar surface;

means for providing a 2-D slice image from said 2-D slice images contained in said first database, wherein said provided 2-D slice image corresponds to the position of said planar surface of said second software object within said augmented 3-D computer model;

means for texture mapping said provided 2-D slice image onto said planar surface of said second software object; and means for displaying an image of said augmented 3-D computer model so as to simultaneously provide a view of both said first software object and said 2-D slice image texture mapped onto said planar surface of said second software object.

2. A visualization system according to claim 1 wherein said 3-D geometry database comprises a surface model.

3. A visualization system according to claim 1 wherein said system further comprises means for inserting a marker into said first database such that said marker will be automatically incorporated into said second database and automatically displayed where appropriate in any image displayed by said system.

4. A visualization system according to claim 3 wherein said system further comprises a margin of pre-determined size associated with said marker.

5. A visualization system according to claim 1 wherein said system further comprises means for automatically determining the periphery of any objects contained in said second database and for identifying the corresponding data points in said first database, whereby the periphery of such objects can be highlighted as appropriate in any image displayed by said system.

6. A visualization system according to claim 1 wherein said scanned structure comprises an anatomical structure.

7. A visualization system comprising:

a first database comprising a plurality of 2-D slice images generated by scanning a structure such that each of said 2-D slice images comprises a cross-sectional view of said structure as taken at a plane extending through said structure, said 2-D slice images being stored in a 2-D data format;

a second database comprising 3-D computer model of said scanned structure, said 3-D computer model being generated from said 2-D slice images contained in said first database, said 3-D computer model comprising at least a first software object representative of at least a portion of said scanned structure, said first software object being defined by a 3-D geometry database;

means for providing a particular 2-D slice image from said first database;

means for generating a second software object and for inserting said second software object into said 3-D computer model such that said second software object co-exists with said first software object within said 3-D computer model so as to augment said 3-D computer model, said second software object being defined by a 3-D geometry database and including a planar surface, and said second software object being inserted into said 3-D computer model so that said planar surface of said second software object is located at the position corresponding to the position of said provided 2-D slice image relative to said scanned structure;

means for texture mapping said provided 2-D slice image onto said planar surface of said second software object; and means for displaying an image of said augmented 3-D computer model so as to simultaneously provide a view of both said first software object and said provided 2-D slice image texture mapped onto said planar surface of said second software object.

8. A visualization system according to claim 7 wherein said 3-D geometry database comprises a surface model.

9. A visualization system according to claim 7 wherein said system further comprises means for inserting a marker into said first database such that said marker will be automatically incorporated into said second database and automatically displayed where appropriate in any image displayed by said system.

10. A visualization system according to claim 9 wherein said system further comprises a margin of predetermined size associated with said marker.

11. A visualization system according to claim 7 wherein said system further comprises means for automatically determining the periphery of any objects contained in said second database and for identifying the corresponding data points in said first database, whereby the periphery of such objects can be highlighted as appropriate in any image displayed by said system.

12. A visualization system according to claim 7 wherein said scanned structure comprises an anatomical structure.

13. A visualization system according to claim 2 wherein said surface model is a polygonal surface model.

14. A visualization system according to claim 8 wherein said surface model is a polygonal surface model.

15. A method for visualizing a structure comprising the following steps:

(a) providing a first database comprising a plurality of 2-D slice images generated by scanning a structure such that each of said 2-D slice images comprises a cross-sectional view of said structure as taken at a plane extending through said structure, said 2-D slice images being stored in a 2-D data format;

(b) providing a second database comprising a 3-D computer model of said scanned structure, said 3-D computer model being generated from said 2-D slice images contained in said first database, said 3-D computer model comprising at least a first software object representative of at least a portion of said scanned structure, said first software object being defined by a 3-D geometry database;

(c) generating a second software object and inserting said second software object into said 3-D computer model such that said second software object co-exists with said first software object within said 3-D computer model so as to augment said 3-D computer model, said second software object being defined by a 3-D geometry database and including a planar surface;

(d) providing a 2-D slice image from said 2-D slice images contained in said first database, wherein said provided 2-D slice image corresponds to the position of said planar surface of said second software object within said augmented 3-D computer model;

(e) texture mapping said provided 2-D slice image onto said planar surface of said second software object; and (f) displaying an image of said augmented 3-D computer model so as to simultaneously provide a view of both said first software object and said 2-D slice image texture mapped onto said planar surface of said second software object.

16. A method for visualizing a structure comprising the following steps:

(a) providing a first database comprising a plurality of 2-D slice images generated by scanning a structure such that each of said 2-D slice images comprises a cross-sectional view of said structure as taken at a plane extending through said structure, said 2-D slice images being stored in a 2-D data format;

(b) providing a second database comprising a 3-D computer model of said scanned structure, said 3-D computer model being generated from said 2-D slice images contained in said first database, said 3-D computer model comprising at least a first software object representative of at least a portion of said scanned structure, said first software object being defined by a 3-D geometry database;

(c) providing a particular 2-D slice image from said first database;

(d) generating a second software object and inserting said second software object into said 3-D computer model such that said second software object co-exists with said first software object within said 3-D computer model so as to augment said 3-D computer model, said second software object being defined by a 3-D geometry database and including a planar surface, and said second software object being inserted into said 3-D computer model so that said planar surface of said second software object is located at the position corresponding to the position of said provided 2-D slice image relative to said scanned structure;

(e) texture mapping said provided 2-D slice image onto said planar surface of said second software object; and (f) displaying an image of said augmented 3-D computer model so as to simultaneously provide a view of both said first software object and said provided 2-D slice image texture mapped onto said planar surface of said second software object.

* * * * *